(12) United States Patent
Furdui et al.

(10) Patent No.: US 9,023,653 B2
(45) Date of Patent: May 5, 2015

(54) METHOD OF LABELING SULFENIC ACID-CONTAINING PROTEINS AND PEPTIDES

(75) Inventors: Cristina M. Furdui, Clemmons, NC (US); Allen W. Tsang, Clemmons, NC (US); Jiang Qian, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 13/594,040

(22) Filed: Aug. 24, 2012

(65) Prior Publication Data

US 2013/0149732 A1 Jun. 13, 2013

Related U.S. Application Data

(60) Provisional application No. 61/533,858, filed on Sep. 13, 2011.

(51) Int. Cl.
| | |
|---|---|
| *G01N 33/58* | (2006.01) |
| *G01N 1/30* | (2006.01) |
| *G01N 33/64* | (2006.01) |
| *C07K 1/13* | (2006.01) |
| *C07K 1/107* | (2006.01) |

(52) U.S. Cl.
CPC ............... *G01N 1/30* (2013.01); *G01N 33/58* (2013.01); *G01N 33/64* (2013.01); *C07K 1/13* (2013.01); *C07K 1/1077* (2013.01)

(58) Field of Classification Search
None
See application file for complete search history.

(56) References Cited

U.S. PATENT DOCUMENTS

2006/0084173 A1* 4/2006 Poole et al. ............. 436/57

OTHER PUBLICATIONS

Charles, Rebecca L. et al; "Protein sulfenation as a redox sensor." Mol. Cell. Proteom. (2007) 6 p. 1473-1484.*
Carballal, Sebastian et al; "Sulfenic acid formation in human serum albumin by hydrogen peroxide and peroxynitrite." Biochemistry (2003) 42 p. 9906-9914.*
Lipinski, Christopher A. et al; "Experimental and computational approaches to estimate solubility and permeability in drug discovery and development settings." Adv. Drug. Del. Rev. (1997) 23 p. 3-25.*
Speers, Anna E. and Cravatt, Benjamin F.; "Profiling enzyme activities in vivo using click chemistry methods." Chem. Biol. (2004) 11 p. 535-546.*
Aucagne, Vincent and Leigh, David A.; "Chemoselective formation of successive tirazole linkages in one pot: click-click chemistry." Org. Lett. (2006) 8(20) p. 4505-4507.*
Entry for fluorescein isothiocyanate in the Sigma Aldrich catalog, downloaded Aug. 15, 2013.*
Chavez, Juan et al; "New role for an old probe: affinity labeling of oxylipid protein conjugates by n'-aminooxymethylcarbonylhydrazino d-biotin." Anal. Chem. (2006) 78 p. 6847-6854.*
Boivin, Jean et al; "A new practical method for the synthesis of acetylenes." Tet. Lett. (1991) 32(39) p. 5321-5324.*
Qian J et al. A simple and effective strategy for labeling cysteine sulfenic acid in proteins by utilization of beta-ketoesters as cleavable probes. Chem. Comm. 2012; 48: 4091-4093.
International Search Report and Written Opinion, PCT/US12/53376, mailed Nov. 16, 2012.

* cited by examiner

*Primary Examiner* — Maury Audet
*Assistant Examiner* — Fred Reynolds
(74) *Attorney, Agent, or Firm* — Myers Bigel Sibley & Sajovec, P.A.

(57) ABSTRACT

A method of labeling a sulfenic acid (—SOH) group of a cysteine residue in a protein; or peptide, comprises contacting said protein or peptide with a beta-ketoester to covalently couple said beta-ketoester to said cysteine residue and form a beta-ketoester-labeled cysteine residue in said protein or peptide.

11 Claims, 4 Drawing Sheets

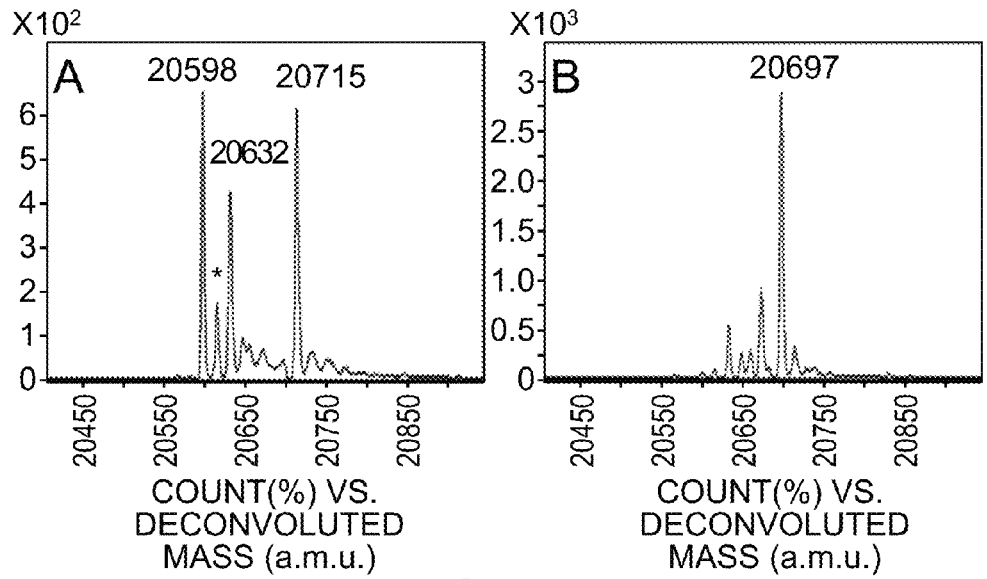
FIG. 1
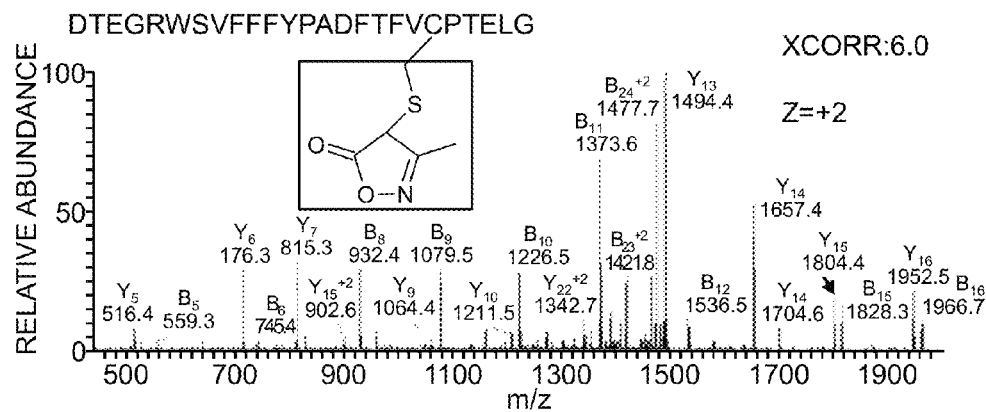
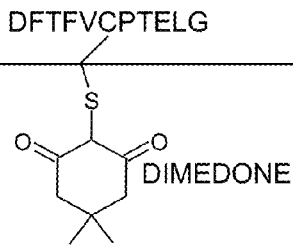
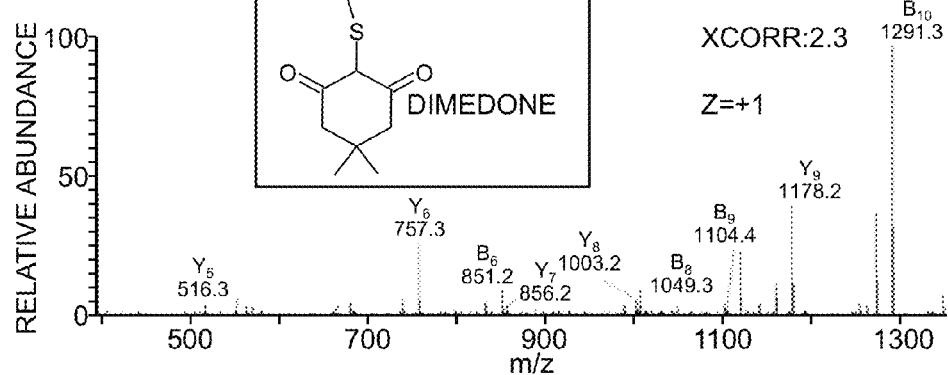
FIG. 2

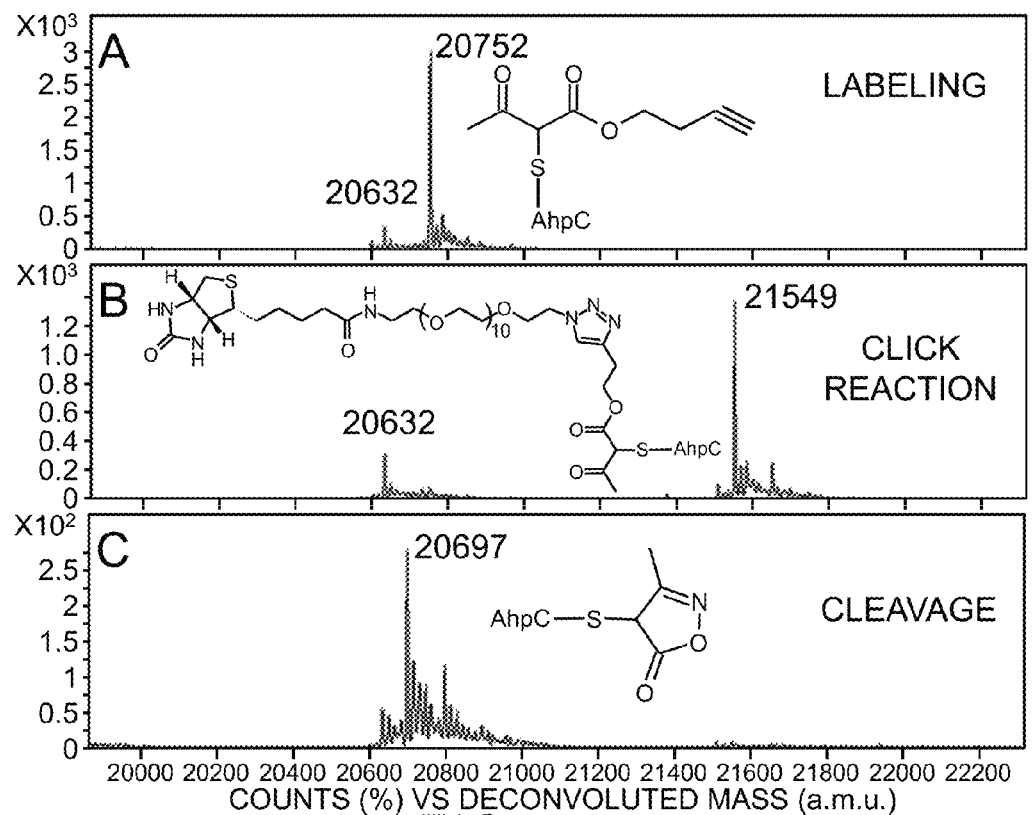
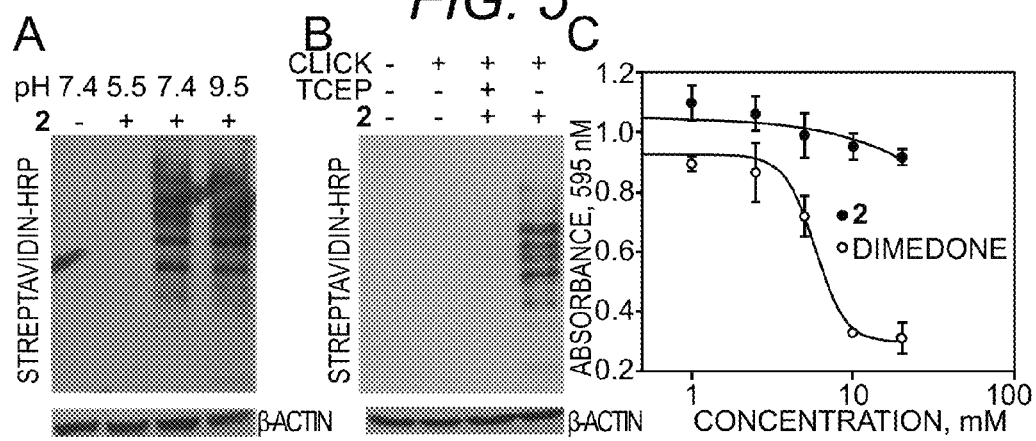
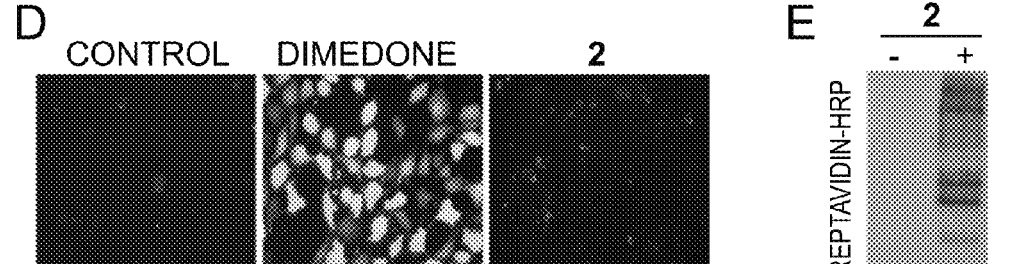
FIG. 6

METHOD OF LABELING SULFENIC ACID-CONTAINING PROTEINS AND PEPTIDES

RELATED APPLICATIONS

This application claims the benefit of U.S. Provisional Application No. 61/533,858; Filed Sep. 13, 2011, the disclosure of which is incorporated by reference herein in its entirety.

STATEMENT REGARDING FEDERALLY SPONSORED RESEARCH

This invention was made with government support under grant number RO1 CA136810 from the National Institutes of Health. The US Government has certain rights to this invention.

STATEMENT REGARDING ELECTRONIC FILING OF A SEQUENCE LISTING

A Sequence Listing in ASCII text format, submitted under 37 C.F.R. §1.821, entitled 9151-171 ST25.txt, 1,148 bytes in size, generated on Dec. 12, 2013 and filed via EFS-Web, is provided in lieu of a paper copy. This Sequence Listing is hereby incorporated herein by reference into the specification for its disclosures.

FIELD OF THE INVENTION

The present invention concerns methods, compositions, and kits useful for labeling or detecting thiol groups in the cysteine residues of proteins that have been oxidized to sulfenic acid.

BACKGROUND OF THE INVENTION

Cysteine thiolate (Cys-S$^-$) is a highly reactive group in proteins serving structural, regulatory and enzymatic functions. A unique reaction that distinguishes thiolates from other protein functional groups is the reversible oxidation by reactive oxygen and nitrogen species (ROS/RNS). Reaction products include thiyl radicals, sulfenic acid (—SOH), disulfides (—S—S—), sulfinic acid (—SO$_2$H) and sulfonic acid (—SO$_3$H) species. The highly reactive thiyl radicals decay rapidly and form disulfides. The metastable—SOH species[1] also favors conversion into more stable species. Disulfides are formed through —SOH reaction with free thiol (—SH) biomolecules like glutathione and cysteines in protein. Additionally, —SOH was shown to react with amine (—NH$_2$) from lysine residues or amide (—NHCO—) in the protein backbone to form sulfenamides (—S—N).[2] Irreversible oxidation to sulfinic and sulfonic states can occur at higher concentrations of ROS. Sulfiredoxin-catalyzed reduction of —SO$_2$H to —SOH in peroxiredoxins is the only currently known exception to this irreversibility[3] On the contrary, —SOH, disulfide and sulfenamide products can be reversibly reduced to —SH by thiol-containing reductants (glutathione, DTT) and phosphines (TCEP).[4] This reversibility is akin to phosphorylation, a critical regulatory protein posttranslational modification. Like phosphorylation, oxidation regulates protein functions[5] and impacts the relay of signaling and metabolic events through redox-mediated processes.[6] The transient nature and reversibility of —SOH in proteins makes their detection challenging. However, given the importance of studying the oxidized proteome, there is an increased interest in developing analytical methods for detection of the —SOH proteins and the sites of cysteine oxidation.[7] Most commonly available methods for selective labeling of —SOH rely on the use of dimedone (5,5-dimethyl-1,3-cyclohexanedione) or dimedone-like derivatives, that have complex synthesis schemes.[8] Facile, two-step synthesis and kinetic characterization of new 1,3-cyclopentanedione-based chemical probes for selective labeling of —SOH in proteins were described recently by the applicants group.[9] The synthesis route relies on highly efficient Michael addition of thiol containing tags or linkers to 4-cyclopentene-1,3-dione, the unsaturated derivative of 1,3-cyclopentanedione.[9-10]

SUMMARY OF THE INVENTION

A first aspect of the invention is a method of labeling a sulfenic acid (—SOH) group of a cysteine residue in a protein or peptide, comprising: contacting the protein or peptide with a beta-ketoester to covalently couple the beta-ketoester to the cysteine residue and form a beta-ketoester-labeled cysteine residue in the protein or peptide.

In some embodiments, the method further comprising the step of detecting the beta-ketoester-labeled cysteine residue in said protein or peptide (e.g., by mass spectrometry).

In some embodiments, the method further comprises the step of coupling a detectable group (e.g., biotin, stable or radioactive isotopes) to the beta-ketoester.

In some embodiments, the method further comprises the step of coupling ligand (e.g., that binds a protein or peptide) to the beta-ketoester (e.g., a member of a specific binding pair).

In some embodiments, the method further comprises the step of detecting the detectable group (e.g., by enzyme assay).

In some embodiments, the method further comprises the step of cleaving said beta-ketoester-labeled cysteine residue (e.g., with hydroxylamine) to produce a 5-isoxazolone-labeled cysteine residue in said protein or peptide.

In some embodiments, the method further comprises the step of detecting the 5-isoxazolone-labeled cysteine residue in the protein or peptide (e.g., by mass spectrometry).

In some embodiments, the contacting step is carried out by contacting the beta-ketoester to a live cell containing said protein or peptide.

A further aspect of the present invention is a beta-ketoester for use in covalently labeling an oxidized sulfenic acid cysteine residue of a protein or peptide.

The present invention is explained in greater detail in the drawings herein and the specification set forth below. The disclosures of all United States Patent references cited herein are to be incorporated by reference herein in their entirety.

BRIEF DESCRIPTION OF THE DRAWINGS

FIG. 1. ESI-TOF MS spectra of C165S AhpC-SOH reaction with 1 (A) and of C165S AhpC labeled with 3-methyl-5-isoxazolone (B). A. Peaks at 20,598, 20,616 (*), 20,632 a.m.u. correspond to sulfenamide (SN), sulfenic acid (—SOH), and sulfinic acid (—SO$_2$H) formation in C165S AhpC, respectively. Labeled adduct peak was observed at a.m.u. 20,714. (AhpC: 50 uM, labeling reagent 1: 5 mM; buffer: 50 mM Bis-tris-citric acid pH 7.4; reaction time: 3 h). B. Disappearance of adduct peak at a.m.u. 20,714 (in A) and appearance of a new peak at 20,697 a.m.u. indicates nearly 100% completion of C165S AhpC-1 adduct cleavage with hydroxylamine treatment. Note: the spectrum in B was generated using C165S AhpC labeled with 1 at pH 8.5 to achieve nearly complete labeling prior to hydroxylamine treatment.

FIG. 2. Positive ion LC-MS/MS spectra of C46 containing peptides in C165S AhpC labeled by 3-methyl-5-isoxazolone after NH₂OH cleavage (top, SEQ ID NO:1), and dimedone (bottom, SEQ ID NO:2). The series of b and y ions confirm the sequence of the AhpC peptide and C46 modification.

FIG. 5. ESI-TOF MS spectra showing the labeling of C165S AhpC-SOH by 2 (adduct peak: 20,752 a.m.u) (A); biotinylation of AhpC-2 adduct via click reaction (adduct peak: 21,549 a.m.u) (B); and, removal of biotin moiety after NH₂OH treatment (adduct peak: 20,697 a.m.u.) (C).

FIG. 6. (A) Labeling of oxidized proteins with 2 at pH 5.5, 7.4 and 9.5 was monitored by Western blot. (B) Selectivity of —SOH labeling with 2 in lysates: cell lysates pre-reduced with TCEP were incubated with 2 at r.t. for 1 h (lane 3). (C) MTT assay to determine cell toxicity. (D) Intracellular ROS level was determined using DCF labeling in NIH 3T3 cells treated with 10 mM dimedone and 2. (E) Cell permeability assay. Cells treated with 2 (10 mM) for 2 h were washed extensively and then lysed in the absence of 2. Click reaction was performed to attach the biotin tag followed by Western blot analysis.

DETAILED DESCRIPTION OF THE PREFERRED EMBODIMENTS

Figure 3:
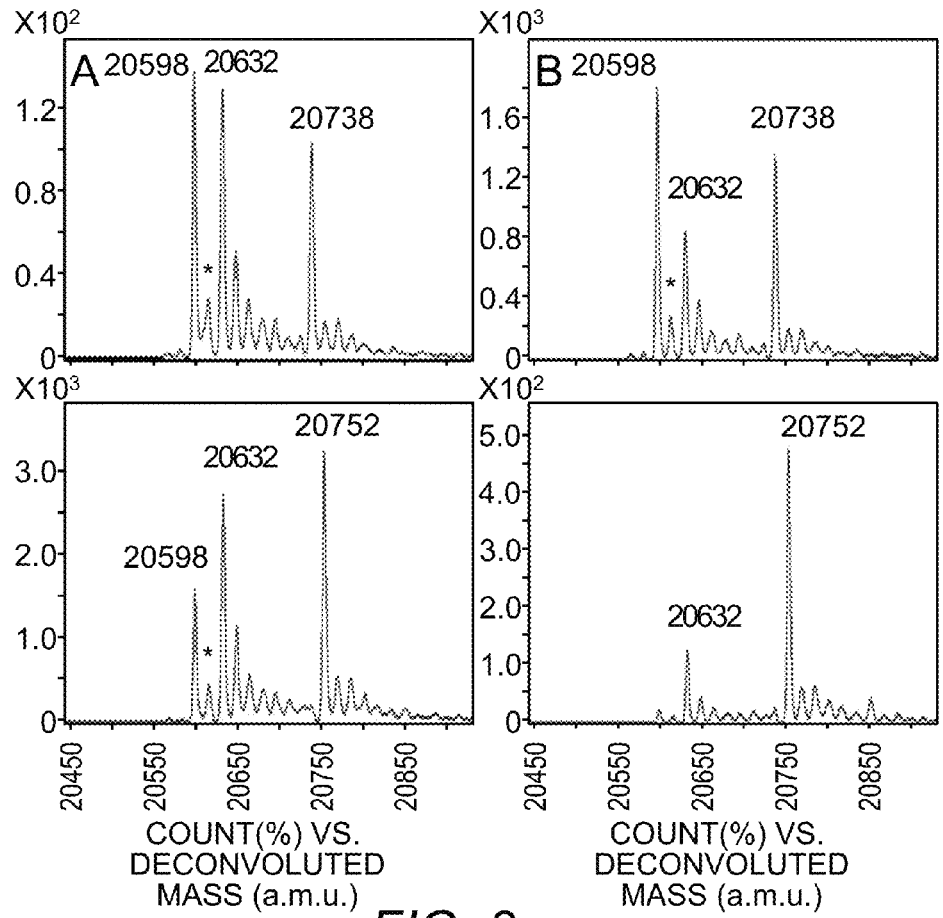
FIG. 3. ESI-TOF MS spectra of C165S AhpC-SOH reaction with dimedone (top) and 2 (bottom) at pH 7.4 (A) and pH 8.5 (B) AhpC adduct peak with dimedone and 2 was observed at 20,738 and 20,752 a.m.u., respectively. Peaks at 20,598, 20,616 (*), 20,632 a.m.u. correspond to sulfenamide (—SN), —SOH, and sulfinic acid (—SO₂H) formation in C165S AhpC, respectively. Note: Sulfenamide is likely formed in gas phase from sulfenic acid after loss of one molecule of H₂O.

"Beta-ketoester" as used herein refers to a compound of the general formula:

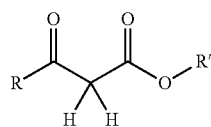

where R and R' may be any suitable organic or inorganic group.

"Sulfenic acid" group of a cysteine residue in a protein or peptide, refers to a group of the formula —SOH, where the bond is to the remainder of the cysteine residue containing the sulfur atom of the group.

"Beta-ketoester-labeled cysteine residue" of a protein or peptide, as used herein, refers to a compound of the formula:

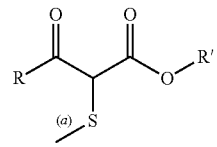

where R and R' may be any suitable group and bond (a) is a bond to the remainder of the cysteine residue in the protein or peptide that contains the sulfur atom shown.

"5-isoxazolone" as used herein for a labeled cysteine residue in a protein or peptide refers to a compound of the formula:

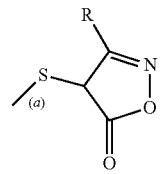

where R may be H or any suitable group, and bond (a) is a bond to the remainder of the cysteine residue in the protein or peptide that contains the sulfur atom shown (note this is our current view of the product structure. However, the applicants do not wish to be bound to any particular theory of the invention, and alternative product structures are to be covered by the current invention).

"Water soluble polymer" as used herein may be any suitable water soluble polymer. Numerous examples are known, including but not limited to poly(ethylene glycol). See, e.g., U.S. Pat. No. 7,910,661 to Kozlowski.

"Linker" or "linking group" as used herein may be a water soluble polymer or any suitable linking group, including but not limited to aromatic, aliphatic, and mixed aromatic/aliphatic groups comprising, consisting of or consisting essentially of C, O, N, P and/or S (e.g., including H where necessary). Numerous examples are known, including but not limited to those described in U.S. Pat. No. 8,247,572.

"Detectable group" as used herein may be any suitable detectable group. Examples include, but are not limited to, enzyme labels, fluorescent labels, radiolabels, antigens, antibodies, etc. See, e.g., U.S. Pat. Nos. 7,723,483; 7,674,584; and 7,351,805. In some embodiments, the detectable group is a member of a specific binding pair. The detectable group may be bound or covalently coupled to other groups such as a beta-ketoester either directly or through a linking group, such as a water soluble polymer.

"Member of a specific binding pair" as used herein may be one partner in any suitable specific binding pair. Examples include, but are not limited to, antibody, antigen, hapten, antihapten, biotin, avidin, streptavidin, IgG, protein A, protein G, drug receptor, drug, toxin receptor, toxin, carbohydrate, lectin, peptide receptor, peptide, protein receptor, protein, carbohydrate receptor, carbohydrate, polynucleotide binding protein, polynucleotide, DNA, RNA, aDNA, aRNA, enzyme, substrate. See, e.g., U.S. Pat. Nos. 8,003,010; 7,985, 539; and 7,939,283. A member of a specific binding pair may be bound or covalently coupled to another compound, such as a beta-ketoester, either directly or through an intermediate linking group, such as a water soluble polymer.

"Labeling" as used herein can be used interchangeably with "covalently coupling" and can be carried out for any purpose, including binding a detectable group to a protein or peptide for detection of that protein or peptide, binding a compound that is itself detectable (e.g., by mass spectrometry) to a protein or peptide, binding or covalently coupling a compound to a protein or peptide for the purpose of inhibiting or enhancing one or more biological functions of activities of that protein or peptide, etc. Other uses and applications of compounds and methods of the present invention include but are not limited to those described in U.S. Pat. No. 7,910,661 to Kozlowski et al. (Nektar Therapeutics) and US Patent Application Publication No. 2010/0009380 to Carroll (University of Michigan).

"Protein or peptide" as used herein may be any suitable protein or peptide, including but not limited to proteins or peptides which are: enzymes (such as metabolic enzymes, protein kinases or phosphatases), receptors (such as G-protein coupled receptors and nuclear hormone receptors), ion channels (such as voltage-gated ion channels and ligand-gated ion channels), transcription factors, hormones, receptor ligands, enzyme substrates, etc.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "lower alkyl" is intended to include both substituted and unsubstituted alkyl or lower alkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating apolyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in lower alkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "lower alkenyl" is intended to include both substituted and unsubstituted alkenyl or lower alkenyl unless otherwise indicated and these groups may be substituted with groups as described in connection with alkyl and lower alkyl above.

"Alkynyl" as used herein alone or as part of another group, refers to a straight or branched chain hydrocarbon containing from 1 to 10 carbon atoms (or in lower alkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "lower alkynyl" is intended to include both substituted and unsubstituted alkynyl or lower alkynyl unless otherwise indicated and these groups may be substituted with the same groups as set forth in connection with alkyl and lower alkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or lower alkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholinesulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

"Amino" as used herein means the —NH$_2$.

"Alkylamino" as used herein alone or as part of another group means the —NHR, where R is an alkyl group.

"Arylalkylamino" as used herein alone or as part of another group means the —NHR, where R is an arylalkyl group.

"Disubstituted-amino" as used herein alone or as part of another group means the —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the —OR, where R is an acyl group as defined herein.

"Ester" as used herein alone or as part of another group refers to —C(O)OR, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compounnd of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfenamide" as used herein alone or as part of another group refers to —SNR$_a$R$_b$, where R$_a$ and R$_b$ are any suitable substituent such as H, alkyl, cycloalkyl, alkenyl, alkynyl or aryl.

"Urea" as used herein alone or as part of another group refers to —N(R$_c$)C(O)NR$_a$R$_b$, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to —N(R$_a$)C(O)OR$_b$, where R$_a$, R$_b$ are any suitable substituent such as H, alkyl, cycloalkyl, alkenyl, alkynyl or aryl.

"Aminoacyloxy" as used herein alone or as part of another group refers to —OC(O)NR$_a$R$_b$, where R$_a$ and R$_b$ are any suitable substituent such as H, alkyl, cycloalkyl, alkenyl, alkynyl or aryl.

Beta-Ketoester Compounds.

Any suitable beta-ketoester can be used to carry out the present invention. Particular examples include, but are not limited to, compounds of Formula I:

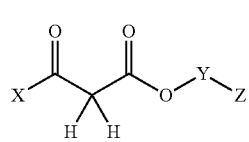

where:

X is any suitable organic or inorganic group, including but not limited to: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

Y is a covalent bond or an alkylene group (e.g., a C1 to C3 or C6 alkylene) or a linker as defined herein; and Z is any suitable organic or inorganic group, including but not limited to: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy.

In some embodiments X is H, alkyl, or a detectable group (e.g., a fluorophore), or an aromatic group (e.g., pyridine, nitrobenzene).

In some embodiments, Z is H, a reactive group (e.g., azide, alkene, alkyne, etc.), or a detectable group (e.g., biotin).

Such compounds may be provided per se or in the form of their physiologically and/or pharmaceutically acceptable salts, depending on how the compound is contacted to the particular protein or peptide for which it is intended.

Contacting of Beta-Ketoesters to Proteins or Peptides.

The step of contacting the beta-ketoester to a protein or peptide can be carried out by any suitable technique. In some embodiments, the protein or peptide is in vitro in a cell-free system, and the contacting step may be carried out by combining the beta-ketoester and the protein or peptide in a solution. In some embodiments, the protein or peptide is in vivo in a cell. The cells may be live cells. The cells may reside in a cell culture or in a tissue or animal containing the cell. The cell may be any suitable cell, including plant or animal cells, animal cells including but not limited to human, cat, dog, horse, rat, pig, rabbit, goat and mouse cells (e.g., skin, muscle, tendon, nerve, liver, lung, pancreatic, cells, etc.). In such embodiments, the beta-ketoester may be added to a culture or growth media containing the cells, or tissue, provided in a pharmaceutically acceptable carrier such as sterile saline solution and administered (e.g., by intraveneous, subcutaneous, or intraperitoneal injection, inhalation, oral administration, etc.) to a subject containing those cells, etc.

Synthesis and Detection of Reporter-Linked Beta-Ketoesters.

In some but not all embodiments of the invention, a reporter or detectable group is linked to the beta-ketoester after it has been bound to the oxidized sulfenic acid cysteine residue.

The step of coupling a chemical group (e.g., reporter or detectable group such as biotin, or chemical groups to enhance selectivity against a desired protein) to the beta-ketoester can be carried out by any suitable means. In one embodiment, the beta-ketoester includes one of a terminal alkyne or an organic azide (e.g., as group "Z" in compounds of Formula I). The detectable group can be coupled to the other of the terminal alkyne or organic azide (directly or through a linking group). The detectable group can then be coupled to the beta-ketoester by "click chemistry" such as described in U.S. Pat. No. 7,375,234 to Sharpless. However, the coupling step can also be carried out by any of a variety of alternate means, including but not limited to those illustrated schematically below, and variations thereof that will be apparent to those skilled in the art based on the present disclosure.

1.

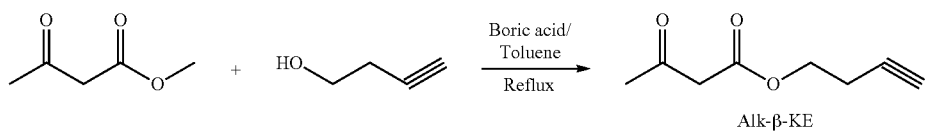

2.

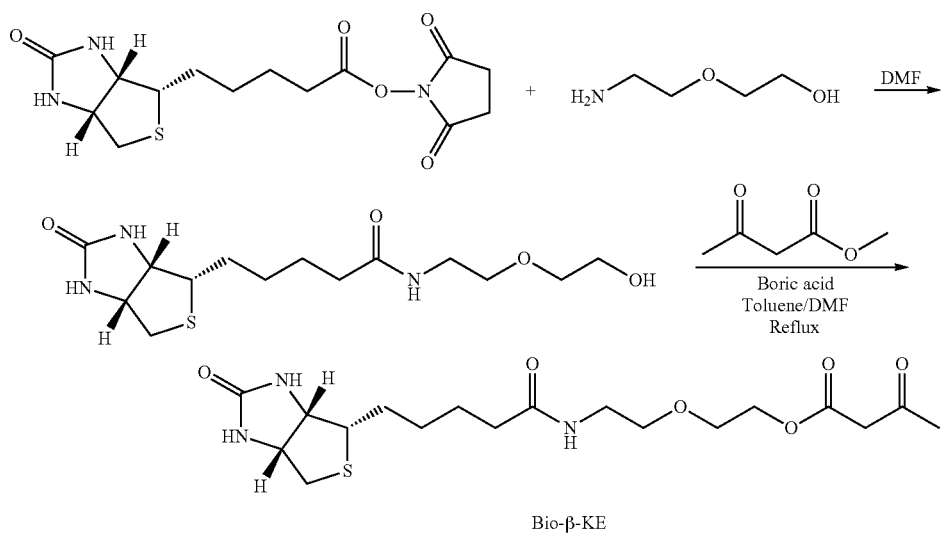

3.

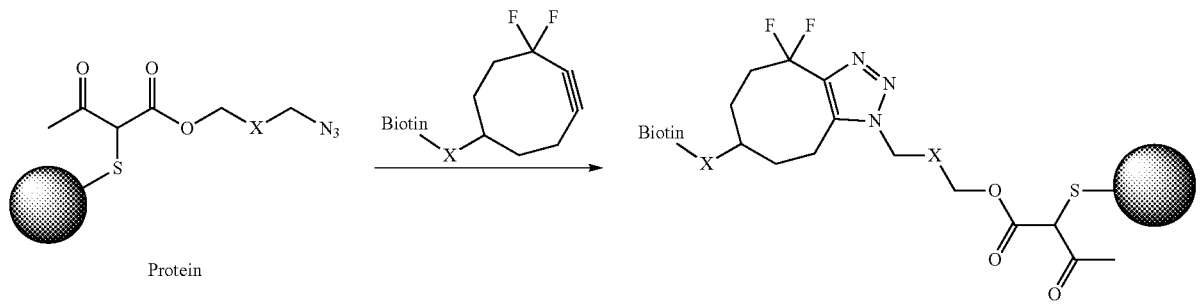

X = Linker

Agard NJ, Prescher JA, Berfozzi CR. (2004) A strain-promoted [3 + 2] azide-alkyne cycloaddition for covalent modification of biomolecules in living systems" *J AM Chem Soc.* 126(46):15046-7, PMID: 15547999

4.
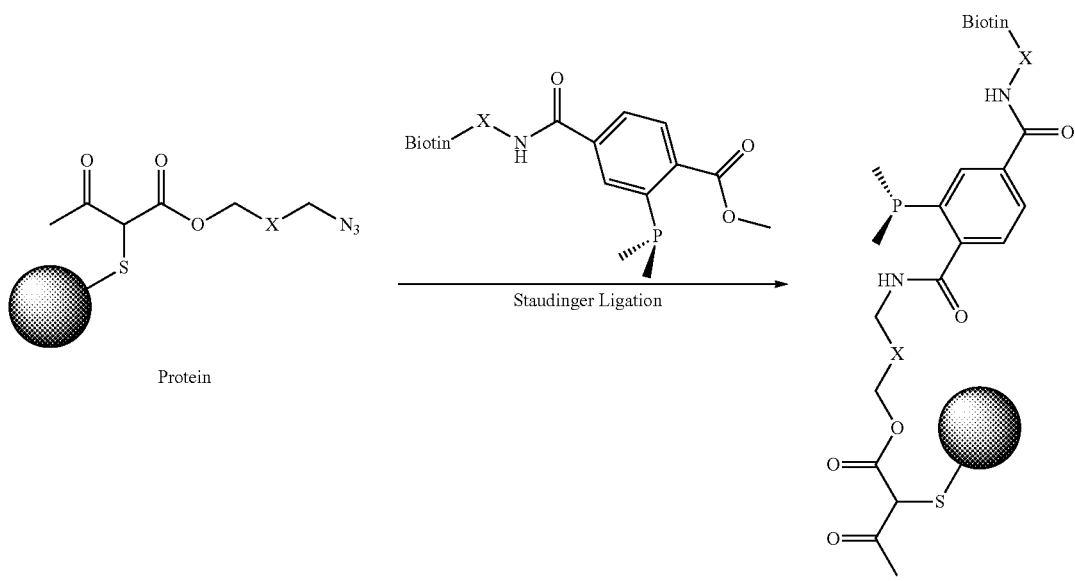
X = Linker
Staudinger, H.; Meyer, J. (1919), "Uber neve organische Phosphorverbindungen III. Phosphlnmethylenderivate und Phoshinlmine", *Helv. Chlm. Acta* 2 (1): 635, dol:10.1002/hica.19190020164
Saxon, E.; Bertozzi, C.R. (2000), "Cell Surface Engineering by a Modified Staudinger Reaction", *Science* 287 (5460): 2007-2010, doi:10.1126/science.287.5460.2007, PMID 10720325.
5.
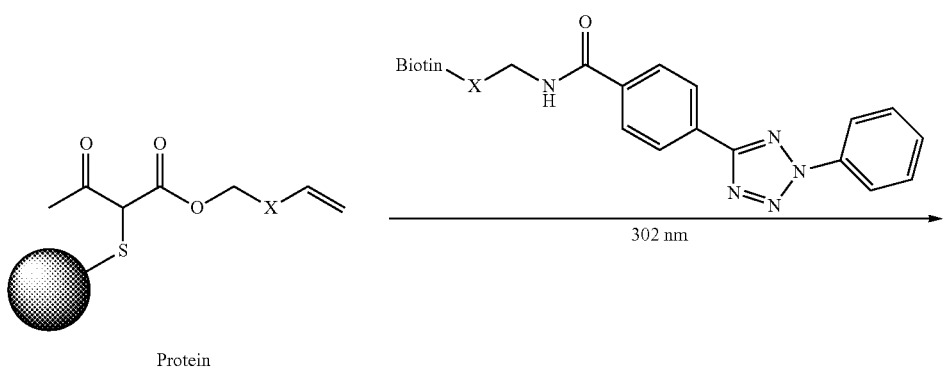

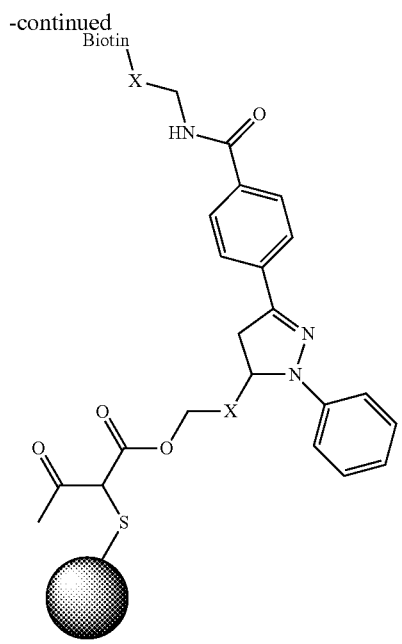

X = Linker

Clovis, James S. (January 1967). "1.3-Dipofare Cycloadditionen, XXV. Der Nachweis des freien Diphenylnitnitifimlns als Zwischenstufe bei Cycloadditionen". *Chemische Berichte* (0009-2940), 100 (1), p. 60.

Wang Y, Vera Cl, Lin Q. (2007) "Convenient synthesis of highly functionalized pyrazolines via mild, photoactivated 1,3-dipolar cycloaddition" *Org Lett.* 2007 Oct. 11;9(21):4155-8.

6.

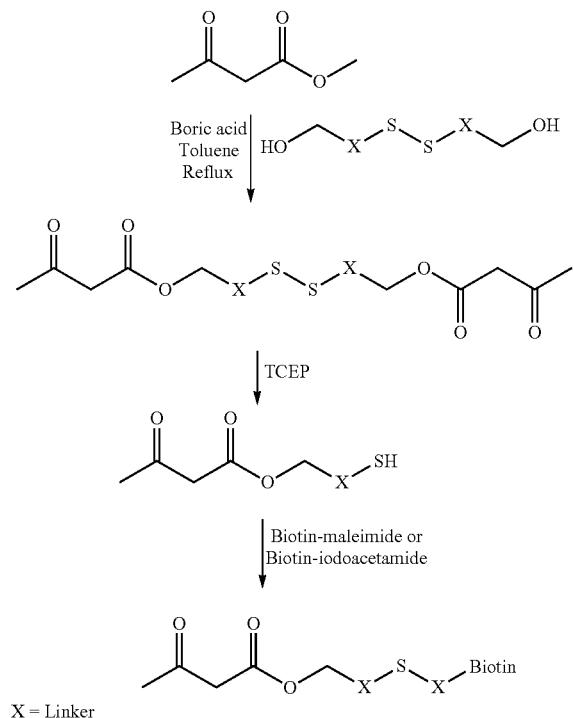

X = Linker

Once the reporter or detectable group is coupled to the beta-ketoester, detection thereof can be carried out in accordance with known techniques as determined by the particular reporter or detectable group employed. Examples of suitable techniques include, but are not limited to, radioassay, enzyme assay, immunoassay, etc.

Detection of Beta-Ketoester Labeled Cysteines; Hydrolysis of Beta-Ketoester.

In some but not all embodiments of the invention, the labeled cysteine is detected by any suitable technique, including but not limited to mass spectrometry. If desired, the beta-ketoester (whether labeled with a reporter or detectable group, or not) can be hydrolyzed (e.g., by contacting to hydroxylamine) to yield a cysteine residue (e.g., in the protein or peptide) that is labeled with a 5-isoxazolone (e.g., a 3-methyl-5-isoxazolone). The 5-isoxazolone can in turn be detected by any suitable technique, including but not limited to mass spectrometry.

The present invention is explained in greater detail in the following non-limiting Examples.

EXAMPLES

Figure 7:
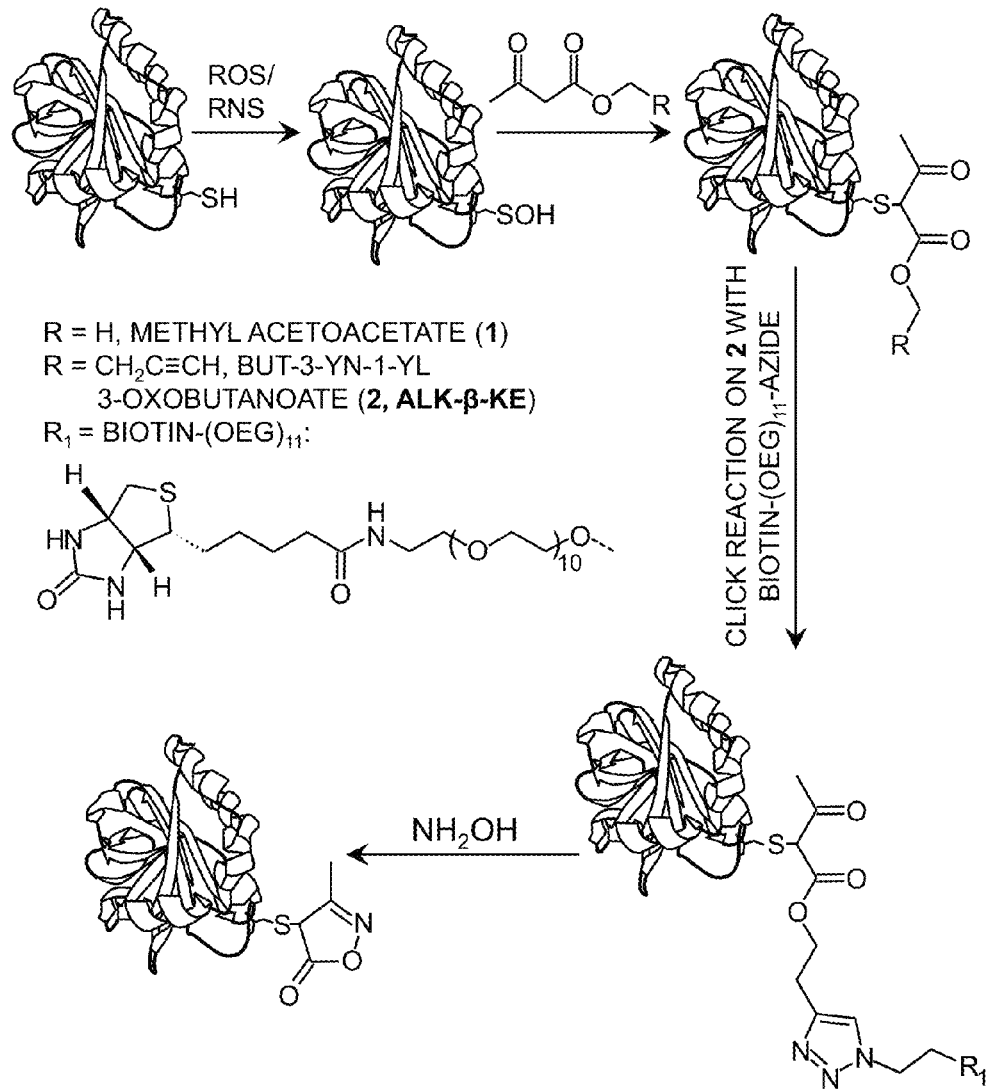
FIG. 7. Reaction of —SOH in proteins with dimedone or β-ketoesters 1 and 2. Proteins labeled by 2 can be conjugated with reporter tags via click-reaction. The reporter tag can then be removed using NH₂OH. The protein structure shown is C165S AhpC and was generated using Swiss PDB Viewer 4.0.1 based on the PDB entry 3EMP.

In this study, we demonstrate that linear β-ketoesters can be utilized as robust chemical probes for labeling and analysis of —SOH modified proteins (FIG. 7). The advantages over the previous reagents are: a. Facile derivatization can be achieved through boric acid-catalyzed transesterification. b. pH dependence of —SOH labeling with β-ketoesters is uniquely distinct from dimedone or 1,3-cyclopentanedione probes with improved reactivity at physiological pH. Moreover, similar to dimedone and 1,3-cyclopentanedione derivatives, the β-ketoester probe discussed here is cell membrane permeable; however, it does not induce accumulation of ROS in the cells and does not cause cell death, important parameters when protein oxidation is studied in cell culture or in vivo.

Initial experiments were performed using methyl acetoacetate (1, in FIG. 7) and AhpC protein. AhpC is a cysteine-based peroxidase from bacteria known to form a stable inter-subunit disulfide bond by condensing the sulfenic acid at reactive C46 with C165 from neighboring AhpC monomers upon oxidation. Mutation of C165 to serine stabilizes the —SOH at C46 and enables reactivity evaluation of chemical probes against this otherwise transient species. C165S AhpC-SOH was prepared as described in the Experimental section. As depicted in FIG. 7, C165S AhpC-SOH was reacted with methyl acetoacetate, 1. The reactivity of 1 with C165S AhpC-SOH was monitored by electrospray ionization time-of-flight MS (ESI-TOF MS).[7] A product peak was observed at 20,714 a.m.u. (FIG. 1A), indicating the labeling of C165S AhpC-SOH by 1. Control experiments showed that 1 did not react with —SH, —S—S—, —$SO_2/_3H$, or other amino acid residues (data not shown). The envisioned advantage of the ester linkage in C165S AhpC-1 was the potential reaction with hydroxylamine ($NH_2OH$) to generate 3-methyl-5-isoxazolone.[8] As anticipated, the yield was nearly quantitative after treatment with 50 mM $NH_2OH$ for 1 h at 37° C. (product peak at 20,697 a.m.u. in FIG. 1B). Further MS analysis confirmed modification of C165S AhpC at C46 with an Xcorr of 6.0 (FIG. 2A) (Xcorr is indicative of the quality of experimental MS/MS fragmentation spectrum of a peptide—a higher number represents a better match with the predicted MS/MS spectrum); by comparison, the Xcorr for the dimedone labeled peptides is much lower, typically between 2 and 3 (FIG. 2B). This could be due to better ionization of the 3-methyl-5-isoxazolone-labeled peptides and/or as a result of lower interference from metal ion chelation, a common problem for diketone-containing molecules[9]

The alkyne analogue of 1 (compound 2 in FIG. 7) was then synthesized via boric acid-catalyzed transesterification[10] (data not shown). Labeling of C165S AhpC-SOH by 2 was compared with dimedone at pH 7.4 and 8.5. Product peaks at a.m.u. 20,738 and 20,752 correspond to dimedone and 2 adducts with C165S AhpC, respectively (FIG. 3). Increased labeling of —SOH with 2 compared with dimedone was observed at both pH 7.4 and 8.5.

Figure 4:
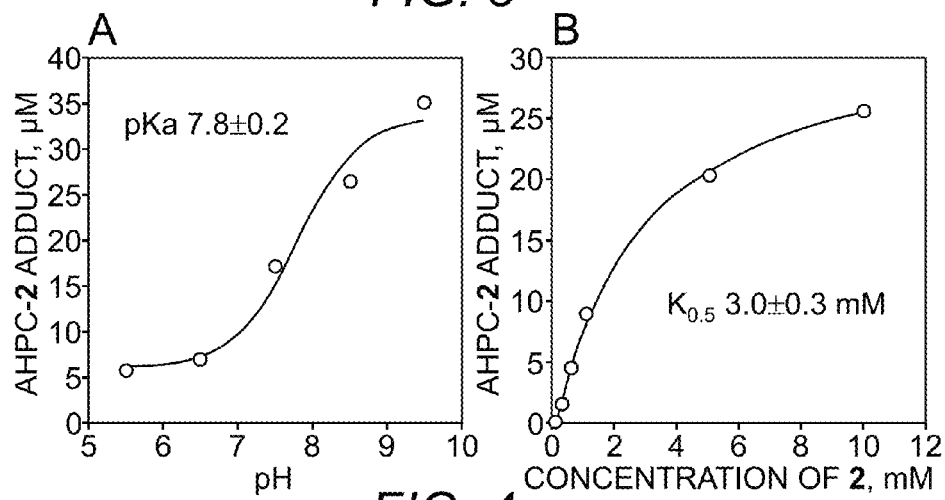
FIG. 4. Plots of C165S AhpC-2 adduct formation as function of pH (A) and concentration of labeling probe 2 (B). The concentration of C165S AhpC-SOH was 50 uM in both (A) and (B); the concentration of 2 was 5 mM in (A) and varied between 0 and 10 mM in (B). The reaction was monitored for 90 mM at r.t. in (A) and 120 min at pH 7.4 in (B). The relative adduct formation was calculated based on its abundance among the total ion abundances of C165S AhpC-SN, —SOH, —SO2H and –2.

Our previous studies using 1,3-cyclopentanedione compounds showed enhanced labeling of AhpC-SOH at lower pH.[7] In contrast, the pH dependence studies of —SOH labeling by 2 showed an increase in the reaction rate at higher pH (FIG. 4A). Data were fit as described in Supporting Material to obtain the pKa 7.8±0.2. This value most likely represents the pKa of the —SOH in C165S AhpC, as the pKa of the ethylene carbon in β-ketoesters is typically much higher (10.6 for 1).[11] This is consistent with the reported values of the —SOH pKa in the range of 6-10.[12] Control experiments using the reduced form of C165S AhpC showed no adduct formation at pH 9.5 (data not shown). The reported pKa for the carbon between keto groups for dimedone and 1 is 4.3 and 10.6, respectively.[11,13] With regard to the keto-enol tautomerism in these compounds, while dimedone was reported to exist exclusively in the enol state,[14] 1 is primarily found in the ketone form (7.4% enol content in aqueous solution).[11] Dimedone showed a slight increase in reactivity at mildly acidic or basic conditions compared to pH 7.4 (data not shown), which can be partly explained by the acid/base-catalyzed enol-formation process.[7] In contrast, 2 reacts very slowly with AhpC-SOH at pH 5.5 and 6.5 but becomes highly reactive as pH increases. These studies suggest that important aspects to consider for the reaction mechanism of this class of probes with —SOH are: a. tautomerism of 1,3-dicarbonyls, b. equilibrium between the —SOH and HS=O tautomers, and c. the pKa at the reactive ethylene carbon in relation to the pH of reaction mixture.

To determine the dependence of labeling reaction on the concentration of 2, the reaction with C165S AhpC-SOH was monitored for 2 h at pH 7.4 using increasing concentrations of 2. There was an increase in the labeling efficiency when the concentration of 2 was increased from 0.2 mM to 5 mM (FIG. 4B). Data were fit to a hyperbolic equation and the $K_{0.5}$ was determined as 3.0±0.3 mM.

To establish the feasibility of our workflow in FIG. 7, the C165S AhpC-2 was then coupled to biotin using the $Cu^+$-catalyzed click reaction. Near 100% conversion was achieved after 1 h reaction at r.t., resulting in a mass increase of 797 a.m.u. (FIG. 5A,B). The removal of the biotin tag was then performed in the presence of $NH_2OH$. The biotin moiety was easily removed to yield the cleaved adduct of C165S AhpC with 100% completion (FIG. 5C). The complete elution of biotin-labeled biomolecules could then be achieved through the $NH_2OH$ cleavage of the biotin tag, a task otherwise difficult in traditional biotin-avidin-based enrichment methods. Moreover, potential complications from the biotin tag in MS analysis would be avoided.

The pH dependence of the labeling reaction was further examined by incubating cell lysates from NIH 3T3 fibroblasts with 2 (5 mM) at pH 5.5, 7.4 and 9.5. Biotin-labeled proteins after click reaction with biotin-$(OEG)_{11}$-azide were visualized using streptavidin-HRP. Nearly equal labeling was observed at pH 7.4 and 9.5, while no visible signal was detected at pH 5.5 (FIG. 6A). The results confirmed the higher reactivity of 2 at pH 7.4 than pH 5.5. Unlike the results with C165S AhpC-SOH, the labeling of lysate proteins was not improved at pH 9.5. This could be explained by considering the instability of —SOH at higher pH in complex cell lysate. The —SOH species may decay and form disulfide bonds with free thiols like glutathione (GSH) or cysteines in proteins since the nucleophilicity of these thiols is also increased at pH 9.5. Also, some of the —SOH proteins may become further oxidized to —$SO_2H$ or —$SO_3H$ under aerobic conditions. The net effect of the enhanced reactivity of 2 at pH 9.5 and the rapid decay of —SOH into other more stable species may result in equal labeling of cellular —SOH proteins at pH 7.4 and pH 9.5. To avoid adventitious oxidation, the follow-up studies were performed at pH 7.4. The selectivity of 2 in labeling —SOH proteins was then examined in cell lysate at pH 7.4.

TCEP is known to reduce —SOH to —SH[3] The results in FIG. 6B demonstrate that 2 does not react with other amino acid residues or functional groups (e.g., glycosyl, phosphoryl, thiols, disulfides, etc.) and is selective towards —SOH in cell lysates.

To test the potential cytotoxicity of 2, cell viability in these experiments was measured using the MTT assay at increasing concentrations of dimedone and 2 (FIG. 6C). Dimedone caused cell death with an IC50 of 5.3±0.2 mM, while 2 did not significantly affect cell viability. Imaging and labeling of ROS with DCF were applied to further determine whether the difference in cytotoxicity could be due to variations in ROS accumulation inside the cells. The DCF assay is a measurement of intracellular ROS level based on the fluorescent intensity observed from cells treated with DCFH-DA (2',7'-dichlorodihydrofluorescein diacetate). A significant increase in ROS was observed when cells were incubated with 10 mM dimedone (FIG. 6D); pre-incubation of cells with 2 did not alter the basal level of ROS (FIG. 6D). Caution should therefore be taken when performing whole-cell labeling experiments or when interpreting results obtained from cells pretreated with dimedone-based probes. Working at dimedone concentrations of 1 mM or lower would be recommended to avoid these artifacts. To assess whether 2 is cell permeable, SCC-61 cells were pretreated with 2 for 2 h, washed repeatedly to remove excess 2, and lysed at pH 7.4. The labeled lysates after the click reaction were analyzed by Western blot. A strong biotin signal was observed when cells were treated with 2, indicating that 2 is cell permeable, similar to dimedone-based probes (FIG. 6E).[15]

In summary, we present here the synthesis and primary evaluation of alkyne β-ketoester probes for labeling of —SOH proteins. These probes display improved kinetics compared to dimedone at pH 7.4; biotin or other tags can be added through the robust click reaction; the tags can be then removed using $NH_2OH$ to yield a derivative amenable for MS analysis. Moreover, we demonstrate that the alkyne fβ-ketoester 2 is cell permeable with minimum effect on the cellular redox status and cell viability. Thus, these compounds have improved properties over 1,3-cyclodione probes and well suited to detect and identify —SOH proteins in vivo and in vitro.

Experimental $^1H$ NMR, $^{13}C$ NMR (300 MHz) spectra were recorded in $CDCl_3$ on a Bruker DPX-300. Synthesized compound was analyzed by Electrospray Ionization (ESI) mass spectrometry (ESI-MS) on a Thermo LTQ instrument. ESI-TOF MS analysis was applied to monitor AhpC labeling by the reagents described here. An Agilent MSD TOF system was used for these studies.

Synthesis of but-3-yn-1-yl 3-oxobutanoate (2)

Methyl acetoacetate (1 g, 8.6 mmol) was dissolved in 40 mL dry toluene. Boric acid (53 mg, 0.86 mmol) and 3-butyn-1-ol (1 g, 14.3 mmol) were added to the methyl acetoacetate/toluene solution under a $N_2$ atmosphere and the mixture was refluxed for 24 hr using a Dean-Stark condenser. Solvents were then removed under reduced pressure. The crude product was purified by flash column chromatography ($SiO_2$, hexane/ethylacetate:15/1) to obtain compound 2 (950 mg, 73% yield), a pale yellow to colorless liquid. $^1H$ NMR 300 MHz (ppm, $CDCl_3$): 4.21 (2H, t J=6.8 Hz), 3.48 (2H, s), 2.59-2.54 (2H, dt J=6.8, 2.7 Hz), 2.29 (3H, s), 2.00 (1H, t J=2.7). $^{13}C$ NMR ($CDCl_3$, 75 MHz): 200.22, 166.83, 79.70, 70.12, 62.99, 49.92, 30.16, 18.89. ESI-MS: $(M+H)^+$=m/z 155.18 (calculated MW of $C_8H_{10}O_3$: 154.16 Da).

Generation of C165S AhpC-SOH Protein.

The C165S AhpC was reduced in 10 mM DTT at room temperature for 30 mM and the DTT was then removed by passing the protein solution through a Bio-Gel spin column equilibrated with $ddH_2O$. The protein concentration was measured based on absorbance at 280 nm using the extinction coefficient 24,300 ($M^{-1} cm^{-1}$). Typically, 200-400 µM C165S AhpC protein was oxidized to —SOH by incubating with 2 equivalents $H_2O_2$ for 1 mM at r.t. with mixing. The excess $H_2O_2$ was removed using Bio-Gel spin columns equilibrated with $ddH_2O$.

C165S AhpC-SOH Labeling with 1 and Reaction with $NH_2OH$.

The C165S AhpC-SOH protein generated as described above was diluted to 50 µM in 50 mM Bis-tris-citric acid buffer (pH 7.4) containing 5 mM (final concentration) of reagent 1. After 3 h incubation with mixing, 30 µL aliquot of reaction mixture was passed through a Bio-Gel column equilibrated with 0.1% formic acid for ESI-TOF MS analysis. For the hydroxylamine cleavage reactions, labeling of C165S AhpC-SOH with 1 was conducted in 50 mM Bis-tris-citric acid buffers (pH 8.5) for 4 h. The covalent C165S AhpC-1 adduct was incubated with 50 mM-1 M hydroxylamine (stock 1N hydroxylamine, pH 8.0-8.5, adjusted by adding 2 N NaOH or 1 N ammonium bicarbonate) for 1 h at 37° C. before passing through the Bio-Gel column for ESI-TOF MS analysis.

Control Experiments Using AhpC-SH, $AhpC-SO_{2/3}H$, and WT AhpC Proteins.

Reduced form of C165S AhpC(C165S AhpC-SH), hyperoxidized protein ($C165S AhpC-SO_2H$ and $—SO_3H$) and WT AhpC (disulfide crosslinked dimer, WT AhpC-S—S-AhpC) in 50 mM Bis-tris-citric acid buffers (pH 7.4) were incubated with 1 (5 mM) for 1.5 h at r.t., pass through the Bio-Gel spin column and analyzed by ESI-TOF MS. $C165S AhpC-SO_2H$ and $—SO_3H$ were generated by incubating C165S AhpC-SH (250 µM) in $ddH_2O$ with 20 equivalents $H_2O_2$ for 1 h at r.t. with mixing. The excess $H_2O_2$ was removed using Bio-Gel spin columns and protein concentration was determined based on absorbance at 280 nm using the extinction coefficient 24,300 ($M^{-1} cm^{-1}$).

C165S AhpC-SOH Labeling with Dimedone and 2.

pH Dependence.

The C165S AhpC-SOH protein was immediately aliquot to appropriate buffers: 50 mM Bis-tris-citric acid pH 7.4, 8.5, and 9.5, and 25 mM critic acid-$Na_2HPO_4$ buffers pH 5.5, and 6.5. Final concentrations of 50 µM protein and 5 mM labeling reagents (dimedone or 2) were used for all reactions. Dimedone stock was made in 0.5 M Bis-tris and DMSO (v:v=1:1) to pre-buffer its acidity around 6.5 before adding it to the reaction buffers. Final DMSO concentration during labeling was 0.5%. At the end of the incubation time (4 h for data in FIG. 1—pH 7.4 and 8.5; 90 min for data in FIG. S5A—pH 5.5-9.5), 30 µl, reaction mixture at each pH was passed through a Bio-Gel spin column and analyzed by ESI-TOF MS. Data were fit using SigmaPlot 11.0 and the user defined equation below to obtain the pKa:

$$Y = \frac{Limit_1 + Limit_2 * 10^{(pH-pKa)}}{10^{(pH-pKa)} + 1}$$

Kinetic Studies.

The C165S AhpC-SOH was incubated with increasing concentrations of 2 (0.2, 0.5, 1, 5, and 10 mM) for 2 h in 50 mM Bis-tris-citric acid (pH 7.4) at r.t. The reaction mixture (30 µL) was passed through a Bio-Gel spin column and analyzed by ESI-TOF MS. Data were fit to a hyperbolic equation to determine $K_{0.5}$ using SigmaPlot 11.0.

Click Reaction to Add the Biotin Tag to C165S AhpC Adduct with 2 (AhpC-2).

C165S AhpC-SOH protein was first labeled by 2 at pH 9.5 for 1 h and passed successively through three Bio-Gel spin columns equilibrated with PBS to remove the unreacted 2. Near 100% labeling of AhpC was configured by ESI-TOF MS. The C165S AhpC-2 adduct concentration was measured at 280 nm using the extinction coefficient 24,300 ($M^{-1}$ $cm^{-1}$) and then diluted in PBS to a final concentration of 50 µM. Click reaction was conducted by adding the following reagents in order: biotin-$OEG_{11}$-azide (1 mM, final, from 50 mM stock in DMSO), TCEP (2 mM, final, from 100 mM stock freshly made in $H_2O$), TBTA (0.1 mM, final, from 1.7 mM stock made in 1:4 DMSO/t-butanol) and $CuSO_4$ (1 mM, final, from 50 mM stock in $H_2O$). The mixture was incubated at r.t. for 2 h and then 30 µL of reaction mixture was passed through a Bio-Gel column equilibrated with 0.1% formic acid for ESI-TOF MS analysis. The biotin moiety was removed by hydroxylamine treatment as described above and the reaction products were analyzed by ESI-TOF MS.

Labeling of —SOH Proteins in NIH 3T3 Cell Lysates with 2.

pH Dependence.

NIH 3T3 cells were cultured to 95% confluence in complete media (DMEM High Glucose (Invitrogen) supplemented with 10% fetal bovine serum (FBS, Invitrogen) and 1% penicillin & streptomycin (Invitrogen)). Cells were washed with PBS three times and lysed using 5 mM of 2 in lysis buffer (50 mM NaCl, 1 mM EDTA, 1 mM EGTA, 10% Glycerol, 1% Triton X-100, 25 mM NaF, 10 µM $ZnCl_2$, supplemented with protease and phosphatase inhibitor tablets (Roche)). Lysis buffer was made in 50 mM citric acid/$Na_2HPO_4$ when labeling was carried out at pH 5.5 and 7.4, and in 50 mM $NaHCO_3$/$Na_2CO_3$ for labeling at pH 9.5. Lysates were incubated for 2 h at r.t. and then quenched by adding cold MeOH/$CHCl_3$[1] to remove excess 2.

Selectivity Studies.

Cells were lysed using lysis buffer (pH 7.4) supplemented with 2 (5 mM) as described above. The labeling was allowed to proceed at r.t. for 2 h before quenching with MeOH/$CHCl_3$. Protein pellets precipitated from 200 µL lysate were resuspended in 50 µL, 1% SDS in PBS, sonicated for 30 s and finally heated at 95° C. for 5 mins. Protein concentration was measured using Bio-Rad protein assay (SDS concentration in the assay 0.001%) and normalized to the same concentration. Click reaction was performed using the solubilized lysate proteins according to the procedures described above. After 2 h incubation, 15 µL reaction aliquot from each sample was mixed with 5 µL sample buffer (with β-mecaptoethanol) for SDS-PAGE and Western blot analysis. Biotinylated proteins were probed using Streptavidin-HRP. In control experiments, lysates were pre-reduced with 10 mM TCEP at pH 7.4 for 1 h at r.t. before the addition of 2; lysates prepared in the absence of 2 with or without click reaction were also included in the SDS-PAGE and Western blot analysis.

DCF Assay.

NIH 3T3 cells cultured in 60-mm dishes were serum starved overnight and incubated with 10 mM dimedone, reagent 2 or 1% DMSO individually for 2 h. 5-(and-6)-carboxy-2',7'-dichloro-dihydrofluorescein diacetate (carboxy-H2DCFDA) (100 µM; Invitrogen) was added to cells at room temperature after the incubation. The cells were then immediately washed twice with PBS and visualized with Arcturus PixCell II laser capture microscope using 20× objective.

Cell Membrane Permeability Assay.

SCC-61 cells were cultured to 95% confluence in complete media (DMEM/F12 High Glucose (Invitrogen) supplemented with 10% fetal bovine serum (FBS, Invitrogen), 1% penicillin & streptomycin (Invitrogen)). Cells were washed with HBSS buffer (pH 7.4) three times and incubated with 10 mM probe 2 in HBSS at r.t. for 2 h. Cells incubated in HBSS without 2 were included as controls. After the incubation, cells were carefully washed by HBSS three times to remove excess 2 and lysed with the lysis buffer described above except in the absence of 2. Lysates were incubated at r.t. for additional 2 h to ensure complete labeling prior to the addition of cold MeOH/$CHCl_3$ for protein precipitation. The denatured proteins were resolubilized in 1% SDS (in PBS) for the click reaction, which was then followed by Western-blot analysis as described above.

MTT Assay.

MTT (3-(4,5-dimethylthiazol-2-yl)-2,5-diphenyltetrazolium bromide) assay was used to test the SCC-61 cell viability when incubated with dimedone or 2 for 1 h. SCC-61 cells were seeded in a 96-well plate at a density of 5,000 per well in 50 µL, and incubated overnight. Dimedone or 2 (50 µL) was added to each well at final concentrations of 1, 2.5, 5, 10, and 20 mM. Plates were then incubated for 1 h at 37° C. in a humidified atmosphere with 5% $CO_2$. MTT labeling reagent (Roche; 5 mg/ml in PBS, 10 µL) was added to each well, and the plate was incubated for 4 h at 37° C. The solubilization solution (100 µL) was then added to each well for overnight incubation at 37° C. The following day, absorbance was measured at 570 nm and all experiments were repeated twice. The resulting curves were fitted using SigmaPlot software to a sigmoidal dose-response equation to determine the IC50. The IC50 represents the concentration of chemical probe causing a 50% reduction in cell viability.

LC-MS/MS Analysis of C165S AhpC Labeled by 3-methyl-5-isoxazolone.

C165S AhpC labeled with 3-methyl-5-isoxazolone was digested using AspN and the resulting peptides were analyzed on a nano-liquid chromatography (LC) system (Dionex Ultimate3000) coupled to a Thermo ESI LTQ mass spectrometer. Peptides were separated using a 60-min gradient of buffer A (0.1% formic acid/97% water/3% acetonitrile, v/v/v) and buffer B (0.1% formic acid/20% water/80% acetonitrile, v/v/v) at a flow rate of 200 mL/min. The LTQ MS was operated in data-dependent acquisition mode using Xcalibur v2.2 (Thermo). After a survey MS scan in the mass range m/z 300-2000, the five most intense precursor ions were isolated and subjected to fragmentation by collision-induced dissociation (CID). The normalized collision energy was set at 35% with activation Q value being 0.25 and dynamic exclusion of 100 s. The acquired raw data were processed using BioWorks software v3.3 (Thermo).

ESI-TOF MS Analysis.

ESI-TOF-MS analysis was performed on Agilent MSD TOF system in positive ion mode with the following settings: capillary voltage (VCap) 3500 V, nebulizer gas 30 psig, drying gas 5.0 L $min^{-1}$; fragmentor 140 V; gas temperature 325° C. The samples were injected at a flow rate of 20 µL $min^{-1}$, using a syringe pump (KD Scientific). The averaged MS spectra were deconvoluted using the Agilent MassHunter Workstation Software v B.01.03.

REFERENCES

[1] [a]G. Roos, J. Messens, *Free Radic Biol Med* 2011, 51, 314-326; [b]C. Jacob et al., *Chem Res Toxicol* 2011.

[2] A. Salmeen et al., *Nature* 2003, 423, 769-773.

[3] D. Mansuy, P. M. Dansette, *Arch. Biochem. Biophys.* 2011, 507, 174-185.

[4] R. Wani et al., *Proc Natl Acad Sci USA* 2011, 108, 10550-10555.

[5] L. B. Poole, K. J. Nelson, *Curr Opin Chem Biol* 2008, 12, 18-24.

[6] [a]R. L. Charles et al., *Mol Cell Proteomics* 2007, 6, 1473-1484; [b]L. B. Poole et al., *Bioconjugate Chem* 2007, 18, 2004-2017; [c]S. E. Leonard et al., *Angew Chem Int Edit.* 2011, 50, 4423-4427; [d]T. H. Truong et al., *Bioorg. Med. Chem. Lett.* 2011.

[7] J. Qian et al., *Chem. Commun. (Camb)* 2011.
[8] N. Jacobsen et al., *Can. J. Chem.* 1984, 62, 1940-1944.
[9] B. J. Hall, J. S. Brodbelt, *J. Am. Soc. Mass. Spectr.* 1999, 10, 402-413.
[10] G. C. M. Kondaiah et al., *Tetrahedron Lett.* 2008, 49, 106-109.
[11] J. W. Bunting, J. P. Kanter, *J. Am. Chem. Soc.* 1993, 115, 11705-11715.
[12] P. Nagy, M. T. Ashby, *J Am Chem Soc* 2007, 129, 14082-14091.
[13] F. M. Wong, J. R. Keeffe, W. M. Wu, *Tetrahedron Lett.* 2002, 43, 3561-3564.
[14] R. J. Cremlyn et al., *Spectrochimica Acta.* 1996, 52, 1423-1432.
[15] Y. H. Seo, K. S. Carroll, *Bioorg. Med. Chem. Lett.* 2009, 19, 356-359.

The foregoing is illustrative of the present invention, and is not to be construed as limiting thereof. The invention is defined by the following claims, with equivalents of the claims to be included therein.

(b), cleaving said beta-ketoester-labeled cysteine residue to produce a 5-isoxazolone-labeled cysteine residue in said protein or peptide;
wherein said beta-ketoester is a compound of Formula I:

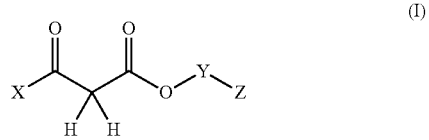

wherein:
X is H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sul-

---

---

That which is claimed is:

1. A method of labeling a sulfenic acid (—SOH) group of a cysteine residue in a protein or peptide, comprising:
   (a) contacting said protein or peptide with a beta-ketoester to covalently couple said beta-ketoester to said cysteine residue and form a beta-ketoester-labeled cysteine residue in said protein or peptide; and then fonate, sulfonic acid, sulfonamide, urea, alkoxylacylamino, aminoacyloxy, or a detectable group;
Y is a covalent bond or an alkylene croup or a linker; and
Z is alkynyl.

2. The method of claim 1, further comprising the step of: detecting said beta-ketoester-labeled cysteine residue in said protein or peptide.

3. The method of claim 1, further comprising the step of coupling a detectable group, or a protein or peptide binding ligand, to said beta-ketoester before said cleaving step.

4. The method of claim 3, further comprising the step of detecting said detectable group.

5. The method of claim 1, further comprising the step of detecting said 5-isoxazolone-labeled cysteine residue in said protein or peptide.

6. The method of claim 1, wherein said contacting step is carried by contacting said beta-ketoester to a live cell containing said protein or peptide.

7. The method of claim 1, wherein said protein or peptide is selected from the group consisting of enzymes, receptors, ion channels, transcription factors, hormones, receptor ligands, and enzyme substrates.

8. The method of claim 1, wherein X is H, alkyl, heterocyclo, aryl, halo, mercapto, azido, formyl, carboxylic acid, acyl, alkylamino, arylalkylamino, or a detectable group.

9. The method of claim 8, wherein X is alkyl.

10. The method of claim 1, wherein said compound of Formula I has the structure:

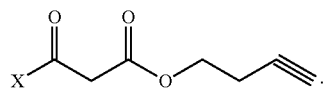

11. The method of claim 10, wherein said compound of Formula I has the structure:

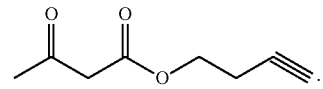

* * * * *

UNITED STATES PATENT AND TRADEMARK OFFICE
CERTIFICATE OF CORRECTION

| | | |
|---|---|---|
| PATENT NO. | : 9,023,653 B2 | Page 1 of 1 |
| APPLICATION NO. | : 13/594040 | |
| DATED | : May 5, 2015 | |
| INVENTOR(S) | : Furdui et al. | |

It is certified that error appears in the above-identified patent and that said Letters Patent is hereby corrected as shown below:

In the Claims:
Column 22, Claim 1, Line 1: Please correct "(b), cleaving"
                                  to read -- (b) cleaving --

Signed and Sealed this
Ninth Day of February, 2016

Michelle K. Lee
*Director of the United States Patent and Trademark Office*

UNITED STATES PATENT AND TRADEMARK OFFICE
CERTIFICATE OF CORRECTION

| | |
|---|---|
| PATENT NO. | : 9,023,653 B2 |
| APPLICATION NO. | : 13/594040 |
| DATED | : May 5, 2015 |
| INVENTOR(S) | : Furdui et al. |

It is certified that error appears in the above-identified patent and that said Letters Patent is hereby corrected as shown below:

In the Specification

Column 1, Lines 15-18: Please delete the paragraph below the STATEMENT REGARDING FEDERALLY SPONSORED RESEARCH and insert the following:
--This invention was made with government support under CA136810 awarded by the National Institutes of Health. The government has certain rights in the invention.--

Signed and Sealed this
Ninth Day of May, 2023

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 25
<212> TYPE: PRT
<213> ORGANISM: Artificial
<220> FEATURE:
<223> OTHER INFORMATION: C46 containing peptide in C165S AhpC sequence
<220> FEATURE:
<221> NAME/KEY: MISC_FEATURE
<222> LOCATION: (20)..(20)
<223> OTHER INFORMATION: Cysteine labeled by 3-methyl-5-isoxazolone
      after hydroxylamine cleavage

<400> SEQUENCE: 1

Asp Thr Glu Gly Arg Trp Ser Val Phe Phe Phe Tyr Pro Ala Asp Phe
1               5                   10                  15

Thr Phe Val Cys Pro Thr Glu Leu Gly
            20                  25

<210> SEQ ID NO 2
<211> LENGTH: 11
<212> TYPE: PRT
<213> ORGANISM: Artificial
<220> FEATURE:
<223> OTHER INFORMATION: C46 containing peptide in C165S AhpC sequence
<220> FEATURE:
<221> NAME/KEY: MISC_FEATURE
<222> LOCATION: (6)..(6)
<223> OTHER INFORMATION: Cysteine labeled with dimedone

<400> SEQUENCE: 2

Asp Phe Thr Phe Val Cys Pro Thr Glu Leu Gly
1               5                   10
```